US011048924B1

(12) United States Patent
Kimura (10) Patent No.: US 11,048,924 B1
(45) Date of Patent: Jun. 29, 2021

(54) ACTION-ESTIMATING DEVICE

(71) Applicant: ASILLA, INC., Tokyo (JP)

(72) Inventor: Daisuke Kimura, Tokyo (JP)

(73) Assignee: ASILLA, INC., Tokyo (JP)

(*) Notice: Subject to any disclaimer, the term of this patent is extended or adjusted under 35 U.S.C. 154(b) by 0 days.

(21) Appl. No.: 17/057,720

(22) PCT Filed: Apr. 9, 2019

(86) PCT No.: PCT/JP2019/015403
§ 371 (c)(1),
(2) Date: Nov. 23, 2020

(87) PCT Pub. No.: WO2019/230199
PCT Pub. Date: Dec. 5, 2019

(30) Foreign Application Priority Data

May 27, 2018 (JP) .............................. JP2018-101097

(51) Int. Cl.
*G06K 9/00* (2006.01)
*G06T 7/73* (2017.01)

(52) U.S. Cl.
CPC ............ *G06K 9/00342* (2013.01); *G06T 7/73* (2017.01); *G06T 2207/10016* (2013.01); *G06T 2207/20076* (2013.01); *G06T 2207/30196* (2013.01)

(58) Field of Classification Search
None
See application file for complete search history.

(56) References Cited

U.S. PATENT DOCUMENTS

| | | | | |
|---|---|---|---|---|
| 2004/0120581 A1* | 6/2004 | Ozer | .................. | G06K 9/00335 382/224 |
| 2007/0132597 A1* | 6/2007 | Rodgers | ................. | H04N 7/141 340/573.1 |
| 2014/0157209 A1* | 6/2014 | Dalal | ................. | G06K 9/00355 715/863 |

FOREIGN PATENT DOCUMENTS

| | | |
|---|---|---|
| JP | 2016-99982 | 5/2016 |
| JP | 2016-170605 | 9/2016 |

(Continued)

OTHER PUBLICATIONS

International Search Report issued in PCT/JP2019/015402, dated Jun. 18, 2019, pp. 1-2.

(Continued)

*Primary Examiner* — Matthew C Bella
*Assistant Examiner* — Brian D Shin
(74) *Attorney, Agent, or Firm* — Jeffrey S. Melcher; Melcher Patent Law PLLC (57) ABSTRACT

[Problem]
To provide an action-estimating device which is capable of estimating an action of a subject appearing in a plurality of time-series images with high precision.
[Solution]
Provided is an action-estimating device 1 comprising: an estimating-side obtaining unit 12 for obtaining a plurality of time-series images Y in which a subject Z appears; an estimating-side detecting unit 13 for detecting a plurality of articulations A appearing in each time-series image Y; an estimating-side measuring unit 14 for measuring coordinates of the detected plurality of articulations A in each time-series image Y; an estimating unit 15 for estimating an action of the subject Z based on displacement of the coordinates of the measured plurality of articulations A in the plurality of time-series images Y; and a storing unit 3 for storing a plurality of choices of the action to be estimated. The estimating-side detecting unit 13 further detects a background appeared in each time-series image Y. In order to estimate the action of the subject Z, the estimating unit 15 calculates a probability of each of the plurality of choices based on the displacement of the coordinates of the measured plurality of articulations A in the plurality of time-series images Y, and corrects the calculated probability of each of the plurality of choices based on the detected background.

6 Claims, 4 Drawing Sheets

(56) References Cited

FOREIGN PATENT DOCUMENTS

| | | |
|---|---|---|
| JP | 2017-102808 | 6/2017 |
| JP | 2017-228100 | 12/2017 |
| JP | 2018-57596 | 4/2018 |
| WO | 2017/61371 | 4/2017 |
| WO | 2019/198696 | 10/2019 |

OTHER PUBLICATIONS

Written Opinion issued in PCT/JP2019/015402, dated Jun. 18, 2019, pp. 1-3.
International Search Report issued in PCT/JP2019/015403, dated Jul. 2, 2019, pp. 1-2, translation included pp. 1-2.
Written Opinion issued in PCT/JP2019/015403, dated Jul. 2, 2019, pp. 1-4, tanslation included pp. 1-2.

* cited by examiner

(a) | WALK : 65% | FALL : 75% | RUN : 45% | PITCH : 65% |

(b) | WALK : 80% | FALL : 85% | RUN : 30% | PITCH : 15% |

(c) | WALK : 80% | FALL : 85% | RUN : — | PITCH : — |

(d) | WALK : 80% | FALL : 95% | RUN : — | PITCH : — |

FIG. 6

ACTION-ESTIMATING DEVICE

TECHNICAL FIELD OF THE INVENTION

The present invention relates to an action-estimating device for estimating an action of a subject appearing in a plurality of time-series images.

BACKGROUND OF THE INVENTION

Conventionally, a device which detects a posture of a human appearing in time-series data based on the articulation of the human appearing in time-series data, and recognizes an action of the human based on the change of the posture is known (for example, Patent Document 1).

PRIOR ART

Patent Document 1: Japanese Patent Application publication No. 2017-228100.

SUMMARY OF INVENTION

Problem to be Solved by the Invention

Generally, in an action-estimating, a highly probable choice is selected from among a plurality of choices based on the detected posture. Therefore, precise selection of the choice will lead to an action-estimating with high accuracy.

In view of the foregoing, it is an object of the invention to provide an action-estimating device for estimating an action of a subject appearing in a plurality of time-series images with high accuracy.

Means for Solving the Problem

The present invention provides an action-estimating device including: an estimating-side obtaining unit configured to obtain a plurality of time-series images in which a subject appears; an estimating-side detecting unit configured to detect a plurality of articulations appearing in each time-series image; an estimating-side measuring unit configured to measure coordinates of the detected plurality of articulations in each time-series image; an estimating unit configured to estimate an action of the subject based on displacement of the coordinates of the measured plurality of articulations in the plurality of time-series images; and a storing unit configured to store a plurality of choices of the action to be estimated. The estimating-side detecting unit further detects a background appeared in each time-series image. In order to estimate the action of the subject, the estimating unit calculates a probability of each of the plurality of choices based on the displacement of the coordinates of the measured plurality of articulations in the plurality of time-series images, and corrects the calculated probability of each of the plurality of choices based on the detected background.

With this configuration, it becomes possible to focus on the action having high probability to occur by considering the background. Therefore, an action estimation with high accuracy can be realized. Further, it becomes possible to decrease the probability of action that is unlikely to occur, while increase the probability of action that is likely to occur. Therefore, an action-estimating with higher accuracy is realized.

It is preferable that the estimating unit excludes one or more choices from among the plurality of choices based on the detected background in order to estimate the action of the subject.

With this configuration, since the number of actions, which is ultimately presented to the user, decreases, it makes easier for the user to recognize the estimated action. In addition, since one or more choices are excluded before calculating the probability of choices, only the probability of choices, which was not excluded, can be calculated efficiently, and then the load on the CPU can be reduced.

It is preferable that the choices whose actions have a relation greater than a prescribed value between each other are associated with each other in the storing unit. When any one of the plurality of choices associated with each other was excluded or the probability of any one of the plurality of choices associated with each other was decreased, the action estimating unit increases the probability of the associated choice which was not excluded or whose probability was not decreased, in order to estimate the action of the subject.

With this configuration, in the case of "pitching" and "fall-down" for example, which have actions look alike part of the way, the probability of the action which was not excluded is increased. Therefore, it makes possible to perform an action estimating with higher accuracy.

Another aspect of the present invention provides an action-estimating program installed on a computer storing a plurality of choices of action to be estimated. The program including: a step for obtaining a plurality of time-series images in which a subject appears; a step for detecting a plurality of articulations appearing in each time-series image; a step for measuring coordinates of the detected plurality of articulations in each time-series image; a step for estimating an action of the subject based on displacement of the coordinates of the measured plurality of articulations in the plurality of time-series images; and a step for detecting a background appeared in each time-series image. In the estimating step, a probability of each of the plurality of choices is calculated based on the displacement of the coordinates of the measured plurality of articulations in the plurality of time-series images, and the calculated probability of each of the plurality of choices is corrected based on the detected background.

It is preferable that, in the estimating step, one or more choices are excluded from among the plurality of choices based on the detected background.

It is preferable that the choices whose actions have a relation greater than a prescribed value between each other are associated with each other in the computer. In the estimating step, when any one of the plurality of choices associated with each other was excluded or the probability of any one of the plurality of choices associated with each other was decreased, the probability of the associated choice which was not excluded or whose probability was not decreased is increased.

Another aspect of the present invention provides an action-estimating device including: an estimating-side obtaining unit configured to obtain a plurality of time-series images in which a subject appears; an estimating-side detecting unit configured to detect a plurality of articulations appearing in each time-series image; an estimating-side measuring unit configured to measure coordinates of the detected plurality of articulations in each time-series image; an estimating unit configured to estimate an action of the subject based on displacement of the coordinates of the measured plurality of articulations in the plurality of time-series images; a setting unit configured to set a purpose or application for the estimating of the action of the subject; and a storing unit configured to store a plurality of choices of the action to be estimated. In order to estimate the action of the subject, the estimating unit calculates a probability of each of the plurality of choices based on the displacement of the coordinates the measured plurality of articulations in the plurality of time-series images, and corrects the calculated probability of each of the plurality of choices based on the set purpose or application.

With this configuration, it becomes possible to focus on the action having high probability to occur by considering the application or purpose. Therefore, an action estimation with high accuracy can be realized. Further, it becomes possible to decrease the probability of action that is unlikely to occur, while increase the probability of action that is likely to occur. Therefore, an action-estimating with higher accuracy is realized.

It is preferable that the estimating unit excludes one or more choices from among the plurality of choices based on the set purpose or application in order to estimate the action of the subject.

It is preferable that the choices whose actions have a relation greater than a prescribed value between each other are associated with each other in the storing unit. When any one of the plurality of choices associated with each other was excluded or the probability of any one of the plurality of choices associated with each other was decreased, the action estimating unit increases the probability of the associated choice which was not excluded or whose probability was not decreased, in order to estimate the action of the subject.

Another aspect of the present invention provides an action-estimating program installed on a computer storing a plurality of choices of action to be estimated and in which a purpose or application for estimating of action of a subject is set including: a step for obtaining a plurality of time-series images in which the subject appears; a step for detecting a plurality of articulations appearing in each time-series image; a step for measuring coordinates of the detected plurality of articulations in each time-series image; and a step for estimating an action of the subject based on displacement of the coordinates of the measured plurality of articulations in the plurality of time-series images. In the estimating step, a probability of each of the plurality of choices is calculated based on the displacement of the coordinates of the measured plurality of articulations in the plurality of time-series images, and the calculated probability of each of the plurality of choices is corrected based on the set purpose or application.

It is preferable that, in the estimating step, one or more choices are excluded from among the plurality of choices based on the set purpose or application.

It is preferable that the choices whose actions have a relation greater than a prescribed value between each other are associated with each other in the computer. In the estimating step, when any one of the plurality of choices associated with each other was excluded or the probability of any one of the plurality of choices associated with each other was decreased, the probability of the associated choice which was not excluded or whose probability was not decreased is increased.

Effects of the Invention

According to the action-estimating device of the present invention, it becomes possible to estimate an action of a subject appearing in a plurality of time-series images with high accuracy.

PREFERRED EMBODIMENTS

An action-estimating device 1 according to a preferred embodiment of the present invention will be described below, while referring to FIGS. 1 to 5.

Figure 1:
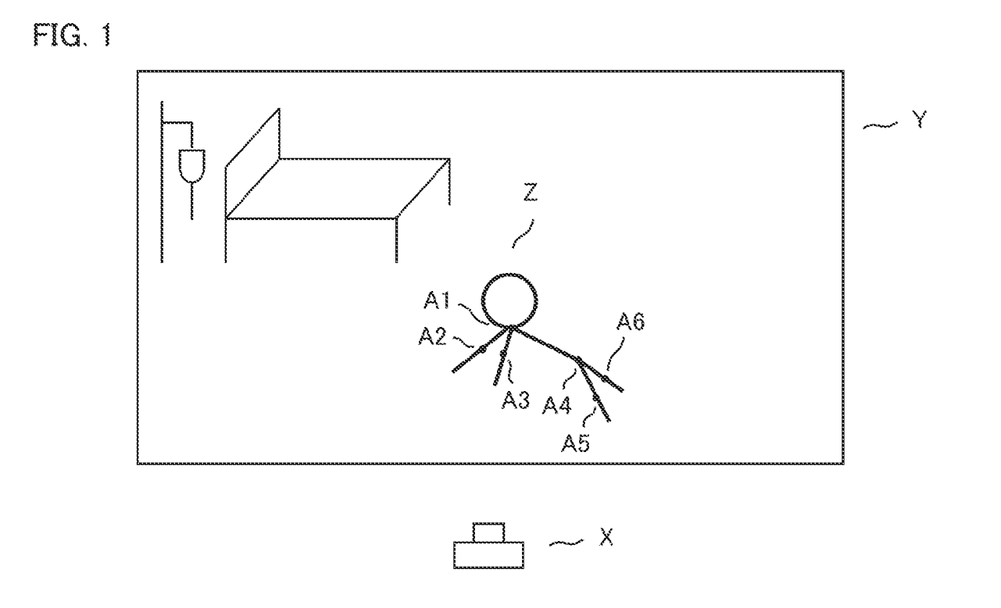
FIG. 1 is an explanatory view of a usage state of the action-estimating device according to an embodiment of the present invention.

As shown in FIG. 1, the action-estimating device 1 is used to estimate an action of a subject Z appearing in a plurality of time-series images Y (e.g., each frame constituting a video or the like) photographed by a photographing means X (in this embodiment, for easy understanding, the subject Z is displayed only on the skeleton). In the action-estimating, information learned by a learning device 2 (see FIG. 2) and stored in a storing unit 3 is referred.

First, the configuration of the learning device 2 is described.

Figure 2:
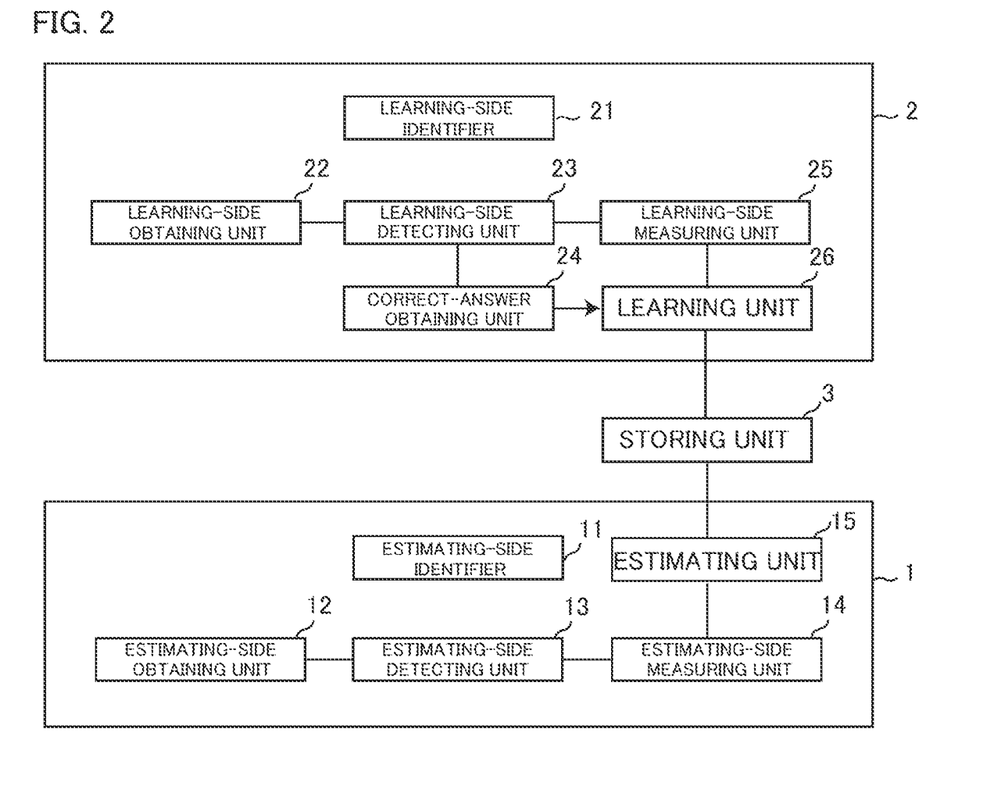
FIG. 2 is a block diagram of a learning device and the action-estimating device according to the embodiment of the present invention.

As shown in FIG. 2, the learning device 2 includes a learning-side identifier 21, a learning-side obtaining unit 22, a learning-side detecting unit 23, a correct-answer obtaining unit 24, a learning-side measuring unit 25, and a learning unit 26.

The learning-side identifier 21 is used to identify a plurality of articulations A (in the present embodiment, neck, right elbow, left elbow, waist, right knee, and left knee) of a subject Z. The learning-side identifier 21 stores articulation-identifying information as references for identifying each articulation A, such as shape, direction, and size. Further, the learning-side identifier 21 also stores supplemental identifying information as references on various "basic posture" ("walking", "stand-up" etc.) of a subject Z, "motion range of each articulation A", and "distance between articulations A."

In addition, the learning-side identifier 21 also stores background identifying information (presence, color, and angle of an object; presence of a person, or the like) as the reference for identifying the background (i.e. "hospital room", "office", "outside" and the like).

The learning-side obtaining unit 22 obtains a plurality of time-series images Y as video images where actions appeared are known. The plurality of time-series images Y is inputted by the user of the action-estimating device 1.

The learning-side detecting unit 23 detects a plurality of articulations A appearing in each time-series image Y. Specifically, the learning-side detecting unit 23 detects the parts corresponding to the articulation-identifying information stored in the learning-side identifier 21, using an inference model modeled by CNN (Convolution Neural Network). Each of the detected articulations A (A1 to A6 in FIG. 1) is selectably displayed on a display unit (not shown).

The learning-side detecting unit 23 also detects backgrounds appeared in each time-series image Y. Particularly, the learning-side detecting unit 23 detects, in each time-series image Y, the part corresponding to the background identifying information stored in the learning-side identifier 21.

The correct-answer obtaining unit 24 obtains a correct action (hereinafter referred to as correct-action) of the subject Z appearing in the plurality of time-series images Y, on each articulation A detected by the learning-side detecting unit 23. The correct-action is inputted by the user of the action-estimating device 1. In particular, as shown in FIG. 1, when the subject Z is falling-down in the plurality of time-series images Y, the user selects each articulation A on the display unit (not shown) and inputs the correct-action "fall-down."

In addition, in the present embodiment, the correct-answer obtaining unit 24 also obtains a correct-background appeared in the plurality of time-series images Y. For example, if the correct-background is a "hospital room", the user will input a "hospital room" tag. Note that the choices of the correct-action and the correct-background are stored in the storing unit 3.

The learning-side measuring unit 25 measures coordinates and depths of the plurality of articulations A detected by the learning-side detecting unit 23. This measurement is performed on each time-series image Y.

For example, the coordinate and the depth of the articulation A1 in the time-series image Y at the time t1 can be expressed such as XA1($t1$), YA1($t1$), ZA1($t1$). The depth is not necessarily expressed using the coordinate and may be expressed as a relative depth in the plurality of time-series images Y. The depth may be measured by the known method. However, a depth of each articulation A, which has been inputted in advance in the correct-answer obtaining unit 24, may also be used. In this case, for example, the learning unit 26 (described later) learns like "When the articulation has this size and angle, the articulation is in XX meters depth."

The learning unit 26 learns the displacement in the plurality of time-series images Y of the coordinate and the depth of the whole of the plurality of articulations A belonging to each subject Z. Specifically, the learning unit 26 specifies the plurality of articulations A belonging to each subject Z selected by the correct-answer obtaining unit 24 as an articulation group B (see FIG. 3), and then, learns the displacement in the plurality of time-series images Y of the coordinate and the depth of the whole of the articulation group B.

Figure 3:
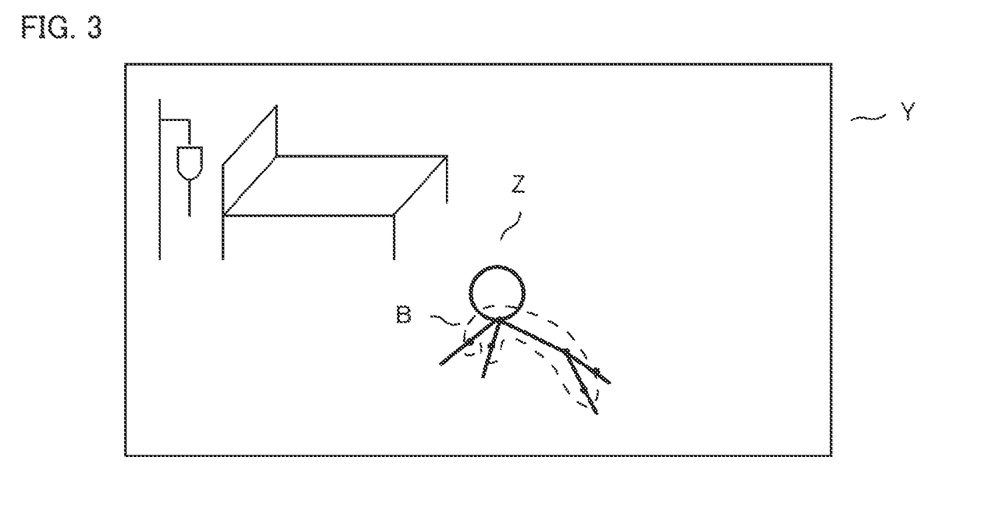
FIG. 3 is an explanatory view of an articulation group according to the embodiment of the present invention.

It is considered to use, as the displacement of the coordinate and the depth of the whole of the articulation group B, the displacement of the coordinate and the depth of the center point of coordinates of all the detected articulations A; or the displacement of the coordinate and the depth of the center of gravity closely related to the body movement. Both of these may also be used to increase the precision. The displacement of the coordinate and the depth of each articulation A may be taken into account to increase the precision. Note that the coordinate and the depth of the center of gravity can be calculated based on the coordinate and the depth of each articulation A and the weight of each articulation A (including muscle, fat, etc.). In this case, information on the weight of each articulation A will be stored in the learning-side identifier 21 or the like in advance.

The learning unit 26 learns the said displacement in the plurality of time-series images Y of the coordinate and the depth of the whole of the articulation group B, in connection with the correct-action inputted in the correct-answer obtaining unit 24. For example, when the correct-action is "fall forward", the displacement of the coordinate of the whole of the articulation group B is learned as "move downward by first distance", and the displacement of the depth of the whole of the articulation group B is learned as "move forward by second distance."

Further, the learning unit 26 learns the background detected by the learning-side detecting unit 23 (the background identifying information) and the correct-background obtained by the correct-answer obtaining unit 24 in association with each other. In this way, it becomes possible to estimate; "The background with such background identifying information is expected to be a hospital room"; "In the case of such background identifying information, the probability for the background to be a hospital room is 80%" and so on.

In addition, in the present embodiment, the learning unit 26 determines the relation between the correct-action and the correct-background, which are obtained by the correct-answer obtaining unit 24. For example, in the case of the background "hospital room", "walking" is most common action, "fall-down" action occurs occasionally, "run" action rarely occurs, and "pitching" action never happens. According to these relations, when the background is "hospital room", for example, it is determined like; "walk: high", "fall-down: middle" "run: low" and "pitching: non". The relations determined as such are stored in the storing unit 3.

It is preferable that the learning unit 26 learns a large amount of images having various viewpoints, other than the plurality of time-series images Y described above. For example, in the case of "hospital room", it is considered that a large amount of images like "hospital rooms photographed at different angles", "hospital rooms having various colored interiors" and "hospital rooms with presence/absence of nurses and patients" are collected to be learned by the learning unit 26.

The storing unit 3 stores various choices of action and background, which the user can select, in the correct-answer obtaining unit 24, other than the above described learning result by the learning unit 26.

Next, the configuration of the action-estimating device 1 will be described as below.

As shown in FIG. 2, the action-estimating device 1 includes an estimating-side identifier 11, an estimating-side obtaining unit 12, an estimating-side detecting unit 13, an estimating-side measuring unit 14, and an estimating unit 15.

The estimating-side identifier 11 is used to identify a plurality of articulations A (in the present embodiment, neck, right elbow, left elbow, waist, right knee, and left knee) of a subject Z. The estimating-side identifier 11 stores articulation-identifying information as references for identifying each articulation A, such as shape, direction, and size. Further, the estimating-side identifier 11 also stores supplemental identifying information as references on various "basic posture" ("walking", "stand-up" etc.) of a subject Z, "motion range of each articulation A", and "distance between articulations A." In the present embodiment, the same information as in the learning-side identifier 21 is stored.

In addition, the estimating-side identifier 11 also stores background identifying information (presence, color, and angle of an object; presence of a person, or the like) as the reference for identifying the background (i.e. "hospital room", "office", "outside" and the like). In the present embodiment, the same information as in the learning-side identifier 21 is stored.

The estimating-side obtaining unit 12 is connected to the photographing means X and obtains video images (i.e., a plurality of time-series images Y) taken by the photographing means X. In the present embodiment, a plurality of time-series images Y is obtained in real-time. However, it may be obtained later depending on the intended purpose of the action-estimating device 1.

The estimating-side detecting unit 13 detects a plurality of articulations A appearing in each time-series image Y. Specifically, the estimating-side detecting unit 13 detects the parts corresponding to the articulation-identifying information stored in the estimating-side identifier 11, using an inference model modeled by CNN (Convolution Neural Network). When the estimating-side detecting unit 13 detects an articulation A, it can be considered that a subject Z appears in the time-series image Y.

The estimating-side detecting unit 13 also detects the background appeared in each of the time-series images Y. In detail, the estimating-side detecting unit 13 detects the parts corresponding to the background identifying information stored in the estimating-side identifier 11 among each of the time-series images Y. Then, the estimating-side detecting unit 13 determines the background while referring to the learning result by the learning unit 26 stored in the storing unit 3. For example, there presented a "bed" and an "infusion" in FIG. 1, so that it is determined as "the background is a hospital room."

The estimating-side measuring unit 14 measures coordinates and depths of the plurality of articulations A detected by the estimating-side detecting unit 13. This measurement is performed on each time-series image Y.

For example, the coordinate and the depth of an articulation A1 at the time t1 in the time-series images Y can be expressed such as XA1 (*t*1), YA1 (*t*1), ZA1 (*t*1). The depth is not necessarily expressed using the coordinate and may be expressed as a relative depth in the plurality of time-series images Y. The depth may be measured by the known method. However, it is possible to specify the depth referring to the learning unit 26 when the learning unit 26 has already learned about the depth.

The estimating unit 15 estimates the action of the subject Z, based on the displacement in the plurality of time-series images Y of the coordinate and the depth of the whole of the articulation group B. Specifically, the estimating unit 15 selects one or more actions with high probability from among various action choices ("fall-down", "walk", "running" and "throwing", etc.), while referring to the learning result by the learning unit 26 stored in the storing unit 3. Thus, in the action-estimating device 1, the coordinate and the depth of the whole of the articulation group B of each subject Z is inputted in a time-series inference model, in which LSTM (Long Short Term Memory) is used, and the action identifying label such as "walking" and "standing" is outputted.

Here, in this embodiment, the estimating unit 15 also considers the background appeared in the time-series images Y in order to estimate the action of the subject Z. In detail, while referring to the relation between the correct-action and the correct-background stored in the storing unit 3, the estimating unit 15 corrects the probability of choices of action, according to the background detected (determined) by the estimating-side detecting unit 13.

Figure 4:
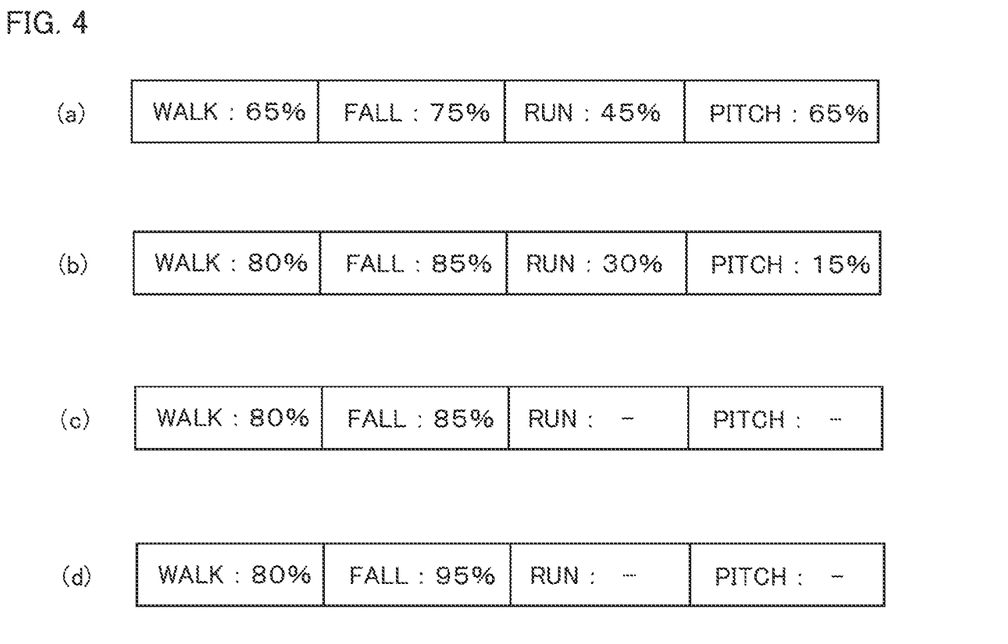
FIG. 4 is an explanatory view of a correction of action choices based on a background according to the embodiment of the present invention.

For example, the case where those probabilities become "walk: 65%", "fall-down: 75%" "run: 45%", and "pitching: 65%" is considered, as shown in FIG. 4 (*a*) if the action of subject Z is estimated without taking into account the background, although the background is "hospital room" actually.

In this case, since "pitching" action is similar to "fall-down" part of the way, the above probability of "pitching" action is estimated highly. However, "pitching" is an action of exceedingly rare to occur in a "hospital room."

Then, in the present embodiment, when those relations are determined as "walk: high", "fall-down: middle" "run: low", and "pitching: non" for "background: hospital room", the probability of the action, which is unlikely to occur in a "hospital room", is corrected downward like "run: from 45% to 30%", and "pitching: from 65% to 15%", as shown in FIG. 4 (*b*). Conversely, the probability of the action, which is likely to occur in a "hospital room", may be corrected upward like "walk: from 65% to 80%", "fall-down: from 75% to 85%".

Further, when the probability of the action, which is unlikely to occur in a "hospital room", is corrected downward and the resulting probability becomes lower than a prescribed value, the action may be excluded from the action choices. For example, under the condition "the action of probability less than 30% is excluded", those actions "run" and "pitching" are excluded, as shown in FIG. 4 (*c*).

Also, actions, such as "fall-down" and "pitching", having a relation greater than a prescribed value between each other may be associated with each other. Then, when any one of the associated actions is excluded or its probability is decreased, the probability of the action of the other may be increased. In the example of FIG. 4, as shown in (d), since "pitching" is excluded, the probability of "fall-down" is increased.

Therefore, since the action-estimating device 1 according to the embodiment considers the background appeared in the time-series images Y in order to estimate the action of subject Z, it becomes possible to perform action estimation with higher accuracy.

Figure 5:
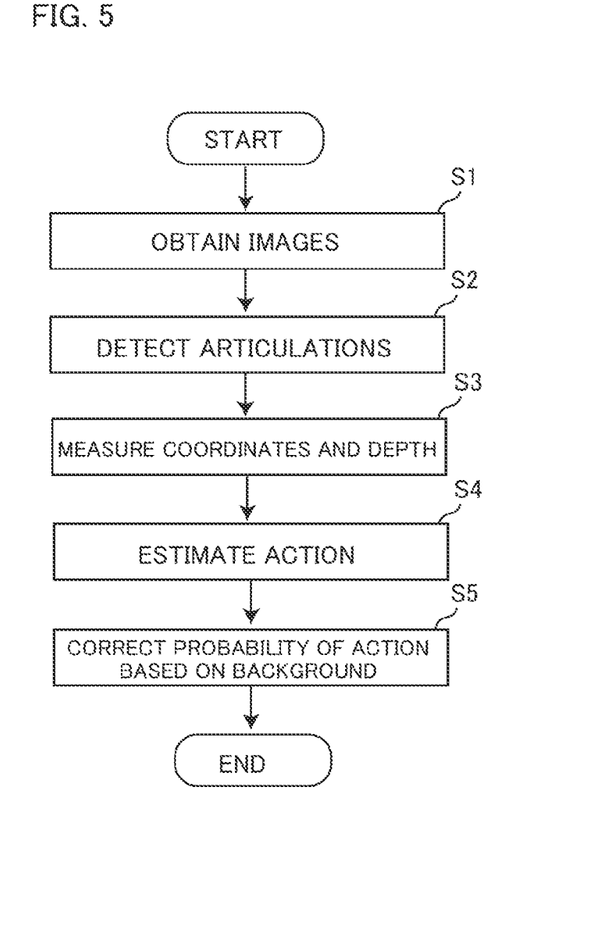
FIG. 5 is a flowchart of an action-estimating in the action-estimating device according to the embodiment of the present invention.

Next, while referring to the flowcharts in FIG. 5, "estimating of action of subject Z" according to the action-estimating device 1 is explained.

First, when a plurality of time-series images Y is obtained by the estimating-side obtaining unit 12 (S1), a plurality of articulations A and backgrounds appearing in each of the time-series images Y are detected by the estimating-side detecting unit 13 (S2).

Next, the coordinates and the depths of the plurality of articulations A detected in S2 are measured by the estimating-side measuring unit 14 (S3). This measurement is performed for each time-series image Y.

Next, the action of subject Z is estimated by the estimating unit 15 based on the displacement in the plurality of time-series images Y of the coordinates and the depths of the plurality of articulations A measured in S3 (S4).

Finally, the probability of the estimated action is corrected based on the detected background (S5).

The action-estimating device 1 having such a configuration, for example, can be used in the below purpose; in a nursing home, the action-estimating device 1 will always photograph inside the room where care-receivers (subject Z)

are there. Then, if the case for those care-receivers to fall or the like are estimated based on the photographed images, the action-estimating device 1 will give an alert on that fact to a caregiver.

As described above, the action-estimating device 1 according to the embodiment considers the backgrounds appeared in the time-series images Y in order to estimate the action of subject Z.

With this configuration, it becomes possible to focus on the action having high probability to occur by considering the background. Therefore, an action estimation with high accuracy can be realized.

Further the action-estimating device 1 according to the present embodiment, in order to estimate the action of the subject Z, calculates the probability of each of the plurality of choices based on the measured displacement in the plurality of time-series images Y of the coordinates of the plurality of articulations A, and corrects the probability of the plurality of calculated choices based on the detected background.

With this configuration, it becomes possible to decrease the probability of action that is unlikely to occur, while increase the probability of action that is likely to occur. Therefore, an action-estimating with higher accuracy is realized.

Further, the action-estimating device 1 according to the embodiment, in order to estimate the action of subject Z, excludes one or more choices from among the plurality of choices, based on the detected background.

With this configuration, since the number of actions, which is ultimately presented to the user, decreases, it makes easier for the user to recognize the estimated action. In addition, since one or more choices are excluded before calculating the probability of choices, only the probability of choices, which was not excluded, can be calculated efficiently, and then the load on the CPU can be reduced.

Further, in the action-estimating device 1 according to the present embodiment, the choices whose actions have a relation greater than a prescribed value between each other are associated with each other. When any one of the plurality of choices associated with each other was excluded or the probability of any one of the plurality of choices associated with each other was decreased, the probability of the associated choice which was not excluded or whose probability was not decreased is increased in order to estimate the action of the subject Z.

With this configuration, in the case of "pitching" and "fall-down" for example, which have actions look alike part of the way, the probability of the action which was not excluded is increased. Therefore, it makes possible to perform an action estimating with higher accuracy.

While the action-estimating device of the invention has been described in detail with reference to the preferred embodiment thereof, it would be apparent to those skilled in the art that many modifications and variations may be made therein without departing from the spirit of the invention, the scope of which is defined by the attached claims.

For example, in the above-described embodiment, though the background is considered in order to estimate the action of the subject Z, application or purpose of the action-estimation may also be take into account.

Figure 6:
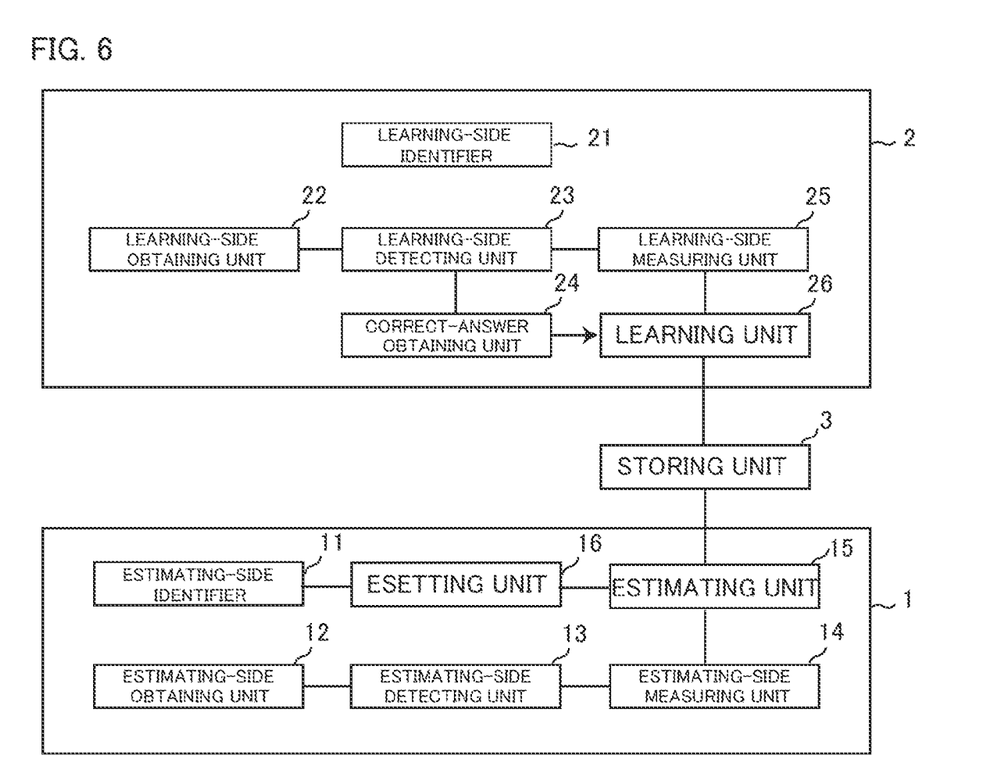
FIG. 6 is an explanatory view of a usage state of the action-estimating device according to a modification of the present invention.

In the case where the purpose is to recognize employees' gesture in an office, for example, since those actions "fall-down," "walking," "running" and "pitching" are inappropriate, the probabilities of those choices are decreased or excluded. On the contrary, those probability of actions like "move of the arms" or "move of the face" can be considered to be increased. In this case, as is shown in FIG. 6, a setting unit 16 is provided to the action-estimating device 1, and the user will set the purpose or the application (crime prevention, medical nursing care etc.). The relation between the correct-action and the purpose or the application are stored in advance in the storing unit 3. When the estimating unit 15 estimates the action of the subject Z, while referring to the said relation, it is possible for the estimating unit 15 to correct the probability of the choices of action, based on the purpose or the application, which is set in the setting unit 16.

Further, in the above embodiment, although the relation between the correct-action and the correct-background, which is learned by the learning unit 26, is stored in the storing unit 3, a set value may also be stored in advance in the storing unit 3.

In the above embodiment, the storing unit 3 is arranged separately from the action-estimating device 1 and the learning unit 2. However, the storing unit 3 may be mounted in the action-estimating device 1 side or in the learning unit 2 side.

In the above embodiment, the displacement in the plurality of time-series images Y of the coordinate and the depth of the articulation group B is considered in order to estimate the action of the subject Z. However, the displacement of each articulation A in the plurality of time-series images Y may be used.

Further, in the above embodiment, the case where the subject Z is a human is explained. However, it is also possible to use the device in order to estimate an animal's action or robot's action. In addition, in the above embodiment, neck, right elbow, left elbow, waist, right knee, and left knee are employed as a plurality of articulations A. However, it is needless to say that the other articulations or more articulations A may also be employed.

The present invention is also applied to a program that conducts the process of the action-estimating device 1, or to a record media accommodating the content of the program. In the case of record media, the program should be installed on the computer or the like. The record media storing the program may be reusable and not one-time use only. As reusable record media, for example, CD-ROM may be employed, but the record media is not limited to this. In addition, it is obvious that a plurality of choices of action to be estimated may be stored in the computer later. Similarly, the purpose or application of the estimation of the targeted action may also be set in the computer later.

DESCRIPTION OF THE REFERENCE NUMBER

1 Action-estimating device
2 Learning device
3 Storing unit
11 Estimating-side identifier
12 Estimating-side obtaining unit
13 Estimating-side detecting unit
14 Estimating-side measuring unit
15 Estimating unit
16 Setting unit
21 Learning-side identifier
22 Learning-side obtaining unit
23 Learning-side detecting unit
24 Correct-answer obtaining unit
25 Learning-side measuring unit
26 Learning unit

The invention claimed is:

1. An action-estimating device comprising:
an estimating-side obtaining unit configured to obtain a plurality of time-series images in which a subject appears;
an estimating-side detecting unit configured to detect a plurality of articulations appearing in each time-series image;
an estimating-side measuring unit configured to measure coordinates of the detected plurality of articulations in each time-series image;
an estimating unit configured to estimate an action of the subject based on displacement of the coordinates of the measured plurality of articulations in the plurality of time-series images; and
a storing unit configured to store a plurality of choices of the action to be estimated,
wherein the estimating-side detecting unit further detects a background appeared in each time-series image, and
wherein, in order to estimate the action of the subject, the estimating unit calculates a probability of each of the plurality of choices based on the displacement of the coordinates of the measured plurality of articulations in the plurality of time-series images, and corrects the calculated probability of each of the plurality of choices based on the detected background.

2. The action-estimating device according to claim 1, wherein the estimating unit excludes one or more choices from among the plurality of choices based on the detected background in order to estimate the action of the subject.

3. The action-estimating device according to claim 1, wherein the choices whose actions have a relation greater than a prescribed value between each other are associated with each other in the storing unit, and
wherein, when any one of the plurality of choices associated with each other was excluded or the probability of any one of the plurality of choices associated with each other was decreased, the action estimating unit increases the probability of the associated choice which was not excluded or whose probability was not decreased, in order to estimate the action of the subject.

4. A method of estimating an action of a subject appearing in a plurality of time-series images by an action-estimating program installed on a computer storing a plurality of choices of action to be estimated comprising:
obtaining a plurality of time-series images in which a subject appears;
detecting a plurality of articulations appearing in each time-series image;
measuring coordinates of the detected plurality of articulations in each time-series image;
estimating an action of the subject based on displacement of the coordinates of the measured plurality of articulations in the plurality of time-series images; and
detecting a background appeared in each time-series image,
wherein, in the estimating step, a probability of each of the plurality of choices is calculated the computer based on the displacement of the coordinates of the measured plurality of articulations in the plurality of time-series images, and the calculated probability of each of the plurality of choices is corrected based on the detected background.

5. The method according to claim 4, wherein, in the estimating step, one or more choices are excluded from among the plurality of choices based on the detected background.

6. The method according to claim 4, wherein the choices whose actions have a relation greater than a prescribed value between each other are associated with each other in the computer,
wherein, in the estimating step, when any one of the plurality of choices associated with each other was excluded or the probability of any one of the plurality of choices associated with each other was decreased, the probability of the associated choice which was not excluded or whose probability was not decreased is increased.

* * * * *